(12) United States Patent
Tampieri et al.

(10) Patent No.: US 9,155,818 B2
(45) Date of Patent: Oct. 13, 2015

(54) CARTILAGINOUS AND OSTEOCHONDRAL SUBSTITUTE COMPRISING MULTILAYER STRUCTURE AND USE THEREOF

(75) Inventors: Anna Tampieri, Faenza (IT); Daniele Pressato, Montegrotto Terme (IT); Claudio De Luca, Padua (IT); Sergio Di Fede, Bologna (IT); Elena Landi, Frazione Toscanella (IT)

(73) Assignee: FIN-CERAMICA FAENZA S.P.A., Faenza (IT)

( * ) Notice: Subject to any disclaimer, the term of this patent is extended or adjusted under 35 U.S.C. 154(b) by 1561 days.

(21) Appl. No.: 11/817,172

(22) PCT Filed: Mar. 2, 2006

(86) PCT No.: PCT/IB2006/000452
§ 371 (c)(1),
(2), (4) Date: Mar. 1, 2008

(87) PCT Pub. No.: WO2006/092718
PCT Pub. Date: Sep. 8, 2006

(65) Prior Publication Data
US 2009/0232875 A1    Sep. 17, 2009

(30) Foreign Application Priority Data

Mar. 4, 2005 (IT) .............................. MI2005A0343

(51) Int. Cl.
*A61L 27/42* (2006.01)
*A61L 27/32* (2006.01)
(Continued)

(52) U.S. Cl.
CPC .............. *A61L 27/425* (2013.01); *A61L 24/102* (2013.01); *A61L 27/24* (2013.01); *A61L 27/26* (2013.01);
(Continued)

(58) Field of Classification Search
CPC ......... A61L 27/46; A61L 27/34; A61L 27/54; A61L 27/12; A61L 27/32; A61L 27/48; A61L 2300/252; A61L 2300/414; A61L 27/26; A61L 27/425; A61L 27/56; A61L 24/102
See application file for complete search history.

(56) References Cited

U.S. PATENT DOCUMENTS 6,117,979 A * 9/2000 Hendriks et al. ............... 530/356
6,585,946 B1 * 7/2003 Bonfield et al. ............... 423/308
(Continued)

FOREIGN PATENT DOCUMENTS

EP    1500405 A1 *  1/2005
JP    06245992 A  *  9/1994
(Continued)

OTHER PUBLICATIONS

Hartgerink et al. "Self-Assembly and Mineralization of Peptide-Amphiphile Nonofibers"; Science, Nov. 23, 2001, vol. 294.*
(Continued)

*Primary Examiner* — Isis Ghali
(74) *Attorney, Agent, or Firm* — Pearne & Gordon LLP

(57) ABSTRACT

The present invention relates to a multilayer structure (1) including a first upper layer (2) consisting of an organic matrix including collagen and at least a lower layer (3, 4, . . . 10) consisting of a composite matrix including hydroxylapatite and collagen. Furthermore, the present invention relates to a cartilaginous substitute including said multilayer structure (1) as well as an osteochondral substitute including said multilayer structure (1). Finally, the present invention relates to the use of said multilayer structure (1) for the preparation of said cartilaginous substitute and said osteochondral substitute for the treatment of cartilaginous defects and osteochondral defects or for the neo-formation of a cartilaginous tissue and/or a subchondral bone tissue.

18 Claims, 14 Drawing Sheets

(51) Int. Cl.
  *A61L 27/34* (2006.01)
  *A61L 27/26* (2006.01)
  *A61L 27/46* (2006.01)
  *A61L 27/54* (2006.01)
  *A61L 27/56* (2006.01)
  *A61L 27/24* (2006.01)
  *A61L 27/48* (2006.01)
  *A61L 24/10* (2006.01)

(52) U.S. Cl.
  CPC ............... *A61L 27/32* (2013.01); *A61L 27/34* (2013.01); *A61L 27/46* (2013.01); *A61L 27/48* (2013.01); *A61L 27/54* (2013.01); *A61L 27/56* (2013.01)

(56) References Cited

U.S. PATENT DOCUMENTS

| | | | | |
|---|---|---|---|---|
| 6,626,950 | B2* | 9/2003 | Brown et al. | 623/23.72 |
| 2003/0114936 | A1* | 6/2003 | Sherwood et al. | 623/23.58 |
| 2005/0043813 | A1 | 2/2005 | Kusanagi et al. | |
| 2005/0074877 | A1* | 4/2005 | Mao | 435/366 |
| 2006/0083728 | A1 | 4/2006 | Kusanagi et al. | |
| 2006/0083729 | A1 | 4/2006 | Kusanagi et al. | |
| 2006/0083730 | A1 | 4/2006 | Kusanagi et al. | |

FOREIGN PATENT DOCUMENTS

| | | | |
|---|---|---|---|
| WO | WO 03022319 A1 * | 3/2003 | |
| WO | WO 2005/018491 A | 3/2005 | |

OTHER PUBLICATIONS

Wang et al. "Tissue engineering of biphasic cartilage constructs using various biodegradable scaffold: an in vitro study", Biomaterials 25 (2004) 3681-3688.*

Baran, E. T.; Tuzlakoglu, K.; Salgado, A. J.; Reis, R. L.: "Multichannel mould processing of 3D structures from microporous coralline hydroxyapatite granules and chitosan support materials for guided tissue regeneration/engineering" Journal of Materials Science: Materials in Medicine, vol. 15, 2004, pp. 161-165, XP002404440.

Sandri, M., et al., "In Vitro Bio-Mineralization Process", 2008, Key Engineering Materials, vol. 361-363I, pp. 543-546.

Tampieri, A., et al., "Biologically Inspired Synthesis of Bone Like Composite: Self-Assembled Collagen Fibers/Hydroxyapatite Nanocrystals", J. Biomed. Mater. Res., vol. 67A; (2003), pp. 618-625.

Tampieri, A., et al., "Design of Graded Biomimetic Osteochondral Composite Scaffolds", Biomaterials 29 (26), 2008, pp. 3539-3546.

Sprio, S., et al., "Hybrid Scaffolds for Tissue Regeneration: Chemotaxis and Physical Confinement As Sources of Biomimesis", Journal of Nanomaterials, vol. 2012, (2012), Article ID 418281, pp. 1-10.

Tampieri, A., et al., "Mimicking Natural Bio-Mineralization Processes: A New Tool for Osteochondral Scaffold Development", Trends in Biotechnology, 2011, vol. 29, pp. 526-535.

Kon, E., et al., "Orderly Osteochondral Regeneration in a Sheep Model Using a Novel Nano-Composite Multilayered Biomaterial", J. Orthop Res. , 2010, vol. 28, pp. 116-124.

Berruto, M., et al., "Treatment of Large Knee Osteochondral Lesions With a Biomimetic Scaffold: Results of a Multicenter Study of 49 Patients At 2-Year Follow-Up", Am J Sports Med, 2014, pp. 1-11.

Delcogliano, M., et al., "Use of Innovative Biomimetic Scaffold in the Treatment for Large Osteochondral Lesions of the Knee", Knee Surg Sports Traumatol Arthrosc, 2013, pp. 1-10.

Kon, E., et al., "Clinical Results and MRI Evolution of a Nano-Composite Multilayered Biomaterial for Osteochondral Regeneration At 5 Years", Am J Sports Med, 2013, pp. 1-8.

Kon, E., et al., "Novel Nano-Composite Multilayered Biomaterial for Osteochondral Regeneration: A Pilot Clinical Trial", The American Journal of Sports Medicine, 2011, pp. 1-11.

* cited by examiner

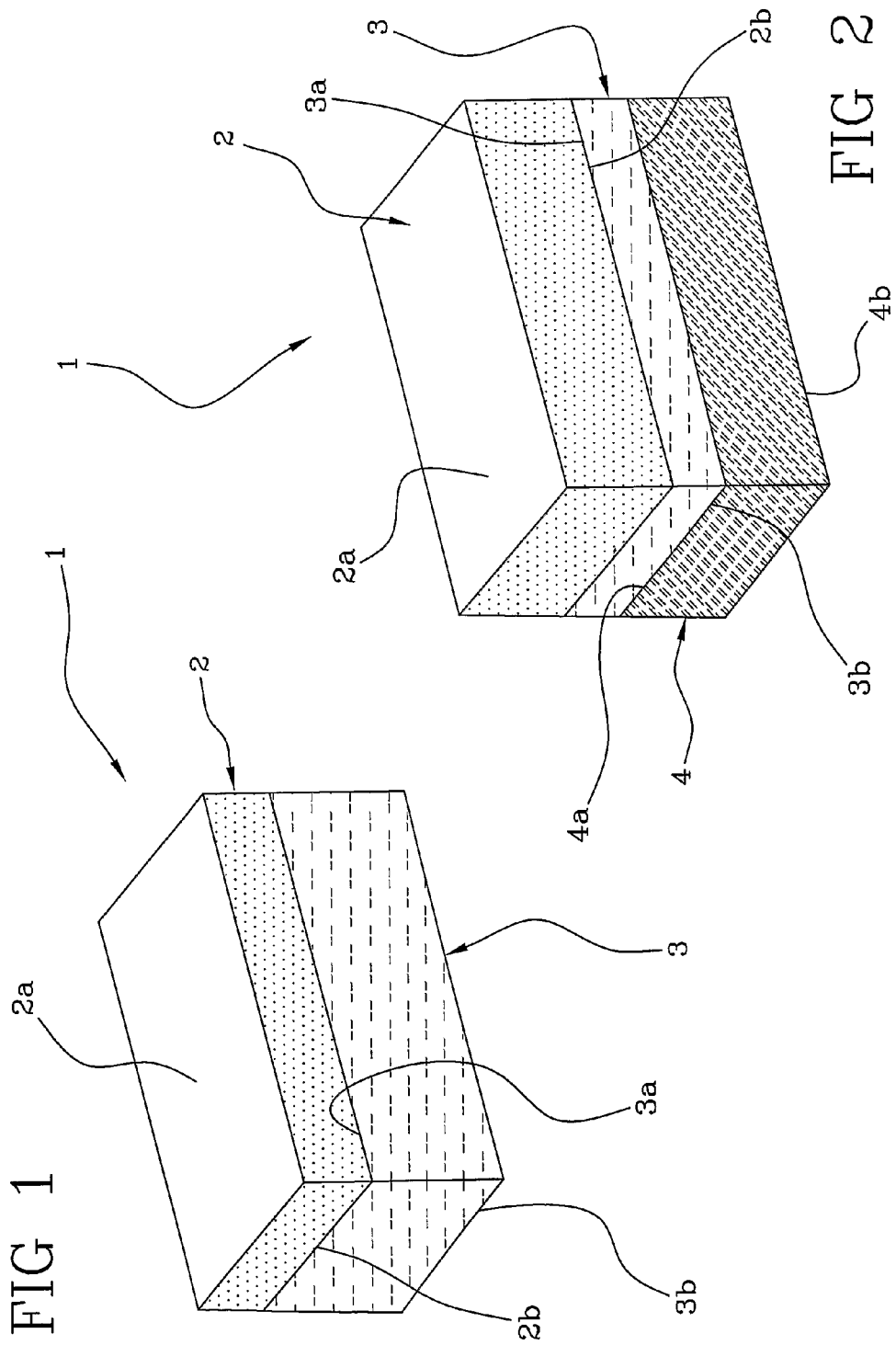

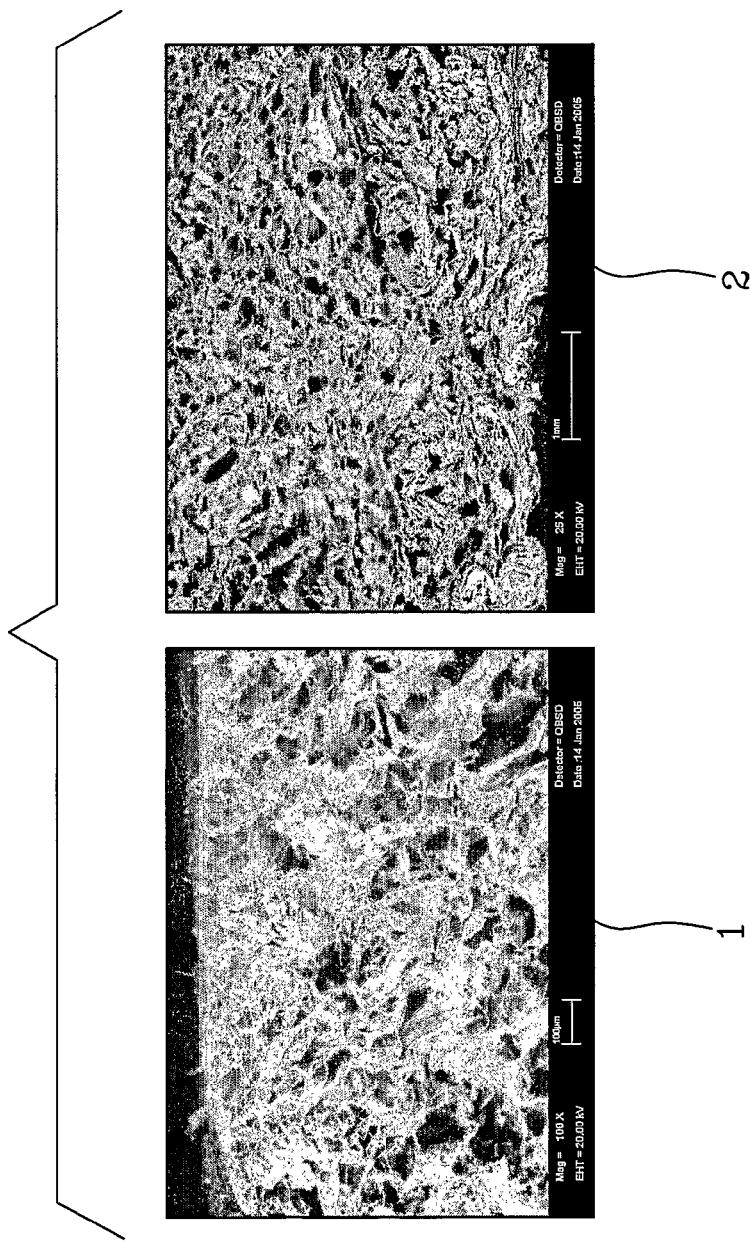

CARTILAGINOUS AND OSTEOCHONDRAL SUBSTITUTE COMPRISING MULTILAYER STRUCTURE AND USE THEREOF

The present invention relates to a multilayer structure including a first upper layer consisting of an organic matrix comprising collagen and at least a lower layer consisting of a composite matrix including hydroxylapatite and collagen. Furthermore, the present invention relates to a cartilaginous substitute including said multilayer structure as well as an osteochondral substitute including said multilayer structure. Finally, the present invention relates to the use of said multilayer structure for the preparation of said cartilaginous substitute and said osteochondral substitute for the treatment of articular cartilaginous defects and osteochondral defects or for the neo-formation of a cartilaginous tissue and/or a subchondral bone tissue.

It is known that the articular cartilage (cartilaginous tissue) is a viscoelastic connective tissue formed by a complex, highly organized, non-vascular structure and free of nerve endings.

The articular cartilage is placed outside the subchondral bone plate close to the joints.

The cartilaginous tissue together with the bone tissue belong to the support skeletal tissues or connective tissues which have high mechanical properties.

The cartilaginous tissue has high specific mechanical-elastic properties which allow to constantly reduce the friction induced by the loads on the articular surface during the normal movement activities of the human body. Moreover, the cartilaginous tissue is able to dissipate the peaks of mechanical stress on the sub-chondral bone.

The connective tissue surrounding the cell cartilaginous component, namely the chondrocytes, (2% of the total volume of the cartilage) is dipped in an extracellular matrix/lattice consisting of collagen, proteoglycans and glycoproteins. For example, 2-40% of the connective tissue includes about: 50-60% of collagen, 25-35% of proteoglycans and 10-15% of glycoproteins.

The collagen molecules are uniformly distributed throughout the tissue and are responsible of its shape and mechanical strength.

The proteoglycans and the glycoproteins bind to the collagen by trapping the water within the matrix. Traumas, inflammatory and degenerative diseases can induce significant damages to the articular cartilage which, in a non negligible percentage, can evolve in chronic arthrosis disease. The cartilaginous tissue subjected to a damage, in particular to a deep damage, has a poor self-reparative ability considering the poorly vascularized anatomic region and the limited replication ability of the chondrocyte cells. The result of the self-reparative process of the cartilage is often a formation of fibrous tissue which certainly can not be compared, in terms of mechanical performances and physiological features, to a normal hyaline cartilage. Accordingly, the alteration of the viscoelastic and mechanical balance can lead to considerable pathological consequences with a following compromission of the articular function and with a pain occurrence, although the cartilaginous degeneration process in most of cases is an asymptomatic phenomenon.

The situation evolves in a more complex way in case of lesions involving the sub-chondral bone structure, when the complete demolition of the cartilaginous layer directly exposes the bone to the mechanical stress of the joint.

In conclusion, between the pathological conditions which can induce nearly always irreversible degenerative processes there may be listed, by mere way of example: the bad alignments (varus and valgoid conditions), the avascular necrosis, the osteoarthritis and the rheumatoid arthritis.

The known surgical techniques currently utilized for the repair of the cartilaginous tissue are of course applied as a function of the dimensions and the depth of the defect.

Some known techniques are stated below in a summary form.

The technique called mosaic-plastic surgery, which consists of the transplant of multiple osteochondral cylinders withdrawn from a healthy cartilaginous zone of the joint not subjected to a load is generally carried out by arthroscopy. The mosaic-plastic surgery can be only suitable for osteochondral defects of small sizes, as such practice can produce some adverse side effects on the donor site.

The technique related to transplants of osteochondral tissue from a donor. This technique shows problems bound to the possible viral transmission, the rejection and the limited availability of tissue from a bank.

The technique related to the transplant of autologous chondrocytes withdrawn from healthy cartilaginous zones not subjected to a load, cultured in vitro and re-injected under a periosteal graft or an impermeable membrane of polymeric origin.

The tissue engineering techniques, wherein the cultured chondrocytes are transported through three-dimensional scaffolds based on synthetic or natural polymers.

So far, these two last techniques allowed to reach sufficiently satisfactory morpho-functional results of the cartilaginous structure present in the articular compartment of the knee.

The repairing of the osteochondral defect, which often represents a pathological condition of a difficult solution for the surgeon, particularly when the subject is a young patient, results more complex. In these conditions, besides the restoration of the cartilaginous layer, it is important the reconstruction of the sub-chondral bone structure.

For the treatment of large osteochondral defects, the use of three-dimensional scaffolds which tend to mime the whole osteochondral compartment has been proposed. Said scaffolds have a complex structure, with well defined composition, porosity, architecture and mechanical properties. The outer surface generally consists of a polymeric layer having a porosity of a macroscopic dimension, while the more internal layer consists of a composite material having a polymeric matrix which incorporates the mineral component (Sherwood J et al. Biomaterials 2002; 23(24):4739).

Therefore, there persists the need of having a medical device to be used as a cartilaginous substitute and osteochondral substitute which does not show the drawbacks of the devices existing in the known art.

In particular, there is the need of having a medical device which can be placed in the cartilaginous and sub-chondral compartment subjected to lesion and/or degeneration.

A first aim of the present invention is to provide novel chondral and osteochondral substitutes having a high biocompatibility as they do not give rise to any inflammatory response and exclude the ability of inducing an immune response from the human body.

Another aim of the present invention is to provide novel substitutes in which there is a composite matrix including collagenous fibres or other kinds of natural and/or synthetic polymers, on which nanodimensional crystals (5-30 nm) of hydroxylapatite are nucleated. Another aim of the present invention is to provide a multilayer structure, capable of miming both the cartilaginous component and the sub-chondral bone component.

Another aim of the present invention is to provide biomimetic structures.

Another aim of the present invention is to provide osteoinductive structures.

Another aim of the present invention is to provide degradable and bio-reabsorbable (with reference above all to the collagenous part) and osteointegrable (with reference above all to the inorganic part of hydroxylapatite) structures.

Another aim of the present invention is to provide a medical device capable of acting as a support (scaffold) for the in situ attachment and differentiation of the undifferentiated mesenchymal cells coming from the subchondral compartment, according to the concept of the guided regeneration of the tissues (Baran E T et al. J Master Sci Mater Med. febbraio 2004; 15(2):161-5).

Another aim of the present invention is to provide a medical device capable of being loaded ex-vivo with a concentrate from medullary blood, with a platelet concentrate (PRP), growth factors or generally with factors capable of promoting the trophism and the cell differentiation, such as TGF, EGF, BMP and other factors.

Another aim of the present invention is to provide a medical device capable of being loaded ex-vivo with undifferentiated mesenchymal cells or maintained in culture for a time period required for the multiplication and/or differentiation in parent cells of the osteoblasts and chondrocytes.

Another aim of the present invention is to provide novel osteochondral and cartilaginous grafts/substitutes which can be: dimensioned and adapted as a function of the dimensions of the cartilaginous or osteochondral damage; loaded with pharmacologically active substances such as, for example, anti-inflammatory corticosteroids, FANS, immunosuppressors, antibiotics, antiblastics, antiproliferatives, antivirals; applied with arthroscopic techniques; fixed with the aid of absorbable and non-absorbable sutures, surgical glues of biological and synthetical origin.

These and other objects which will result apparent from the following detailed description are attained by the Applicant, which has carried out a multilayer structure as well as a cartilaginous and osteochondral substitute including said multilayer structure, having the features stated in the appended independent claim. An object of the present invention is a multilayer structure including a first upper layer consisting of an organic matrix including collagen and at least a lower layer consisting of a composite matrix including hydroxylapatite and collagen.

Another object of the present invention is a cartilaginous substitute including said multilayer structure.

A further object of the present invention is an osteochondral substitute including said multilayer structure.

Another object of the present invention is the use of said multilayer structure for the preparation of said cartilaginous substitute and said osteochondral substitute for the treatment of articular cartilaginous defects and osteochondral defects.

Finally, another object of the present invention is the use of said multilayer structure for the neo-formation of a cartilaginous tissue and/or the formation of a sub-chondral bone tissue.

BRIEF DESCRIPTION OF THE DRAWINGS

Further features and advantages of the present invention will better result from the indicative, and therefore not limiting description of a preferred but not exclusive embodiment of a cartilaginous and osteochondral substitute, as it is shown in the enclosed drawings, in which:

FIG. 1 shows a diagrammatic perspective view of a multilayer structure according to a first embodiment;

FIG. 2 shows a diagrammatic perspective view of a multilayer structure according to a second embodiment;

FIG. 7 shows the porous collagenous structure of the prototype D' subjected to crosslinking through glutaraldehyde vapours treatment. Image (1) shows the porous structure of the collagenous layer; image (2) shows an interface between collagenous layer—gradient HA/collagen;

DETAILED DESCRIPTION OF PREFERRED EMBODIMENTS OF THE INVENTION

Figure 3:
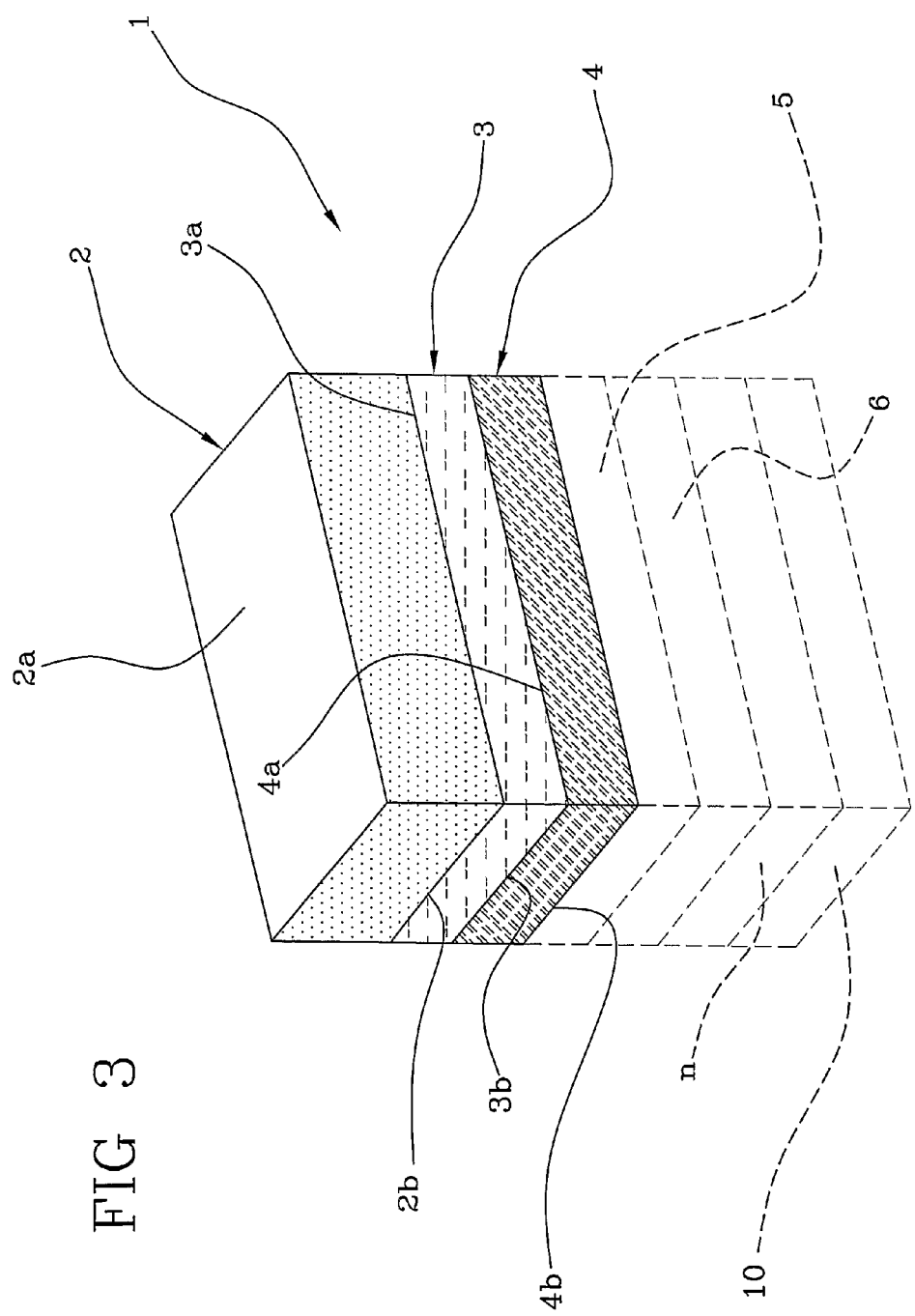
FIG. 3 shows a diagrammatic perspective view of a multilayer structure according to a third embodiment.

The multilayer structure 1, subject of the present invention, includes a first upper layer 2 presenting an upper surface 2a and a lower surface 2b.

As it is shown in FIG. 1, said multilayer structure 1 further includes at least a lower layer 3 associated with said upper layer 2.

In particular, the lower layer 3 includes an upper surface 3a associated with said lower surface 2b of said upper layer 2, and a lower surface 3b opposite to said upper surface 3a.

In a preferred embodiment of the present invention, shown in FIG. 2, two lower layers 3, 4 can be foreseen. In this situation, the lower layer 3 close to the upper layer 2 presents a respective upper surface 3a associated with said lower surface 2b of the upper layer 2 and a lower surface 3b associated with an upper surface 5a of the lower layer 4.

Advantageously, in this situation the lower layer 3 forms an intermediate layer arranged between said upper layer 2 and said lower layer 4.

Within the ambit of the present invention, multilayer structures 1, including a plurality of lower layers, for example in a number greater than two and smaller or equal to ten, are included.

For example, as it is shown in FIG. 3, the multilayer structure 1 can show four lower layers 3, 4, 5 and 6, each of which showing a respective upper surface associated with the lower surface of the adjacent layer.

The upper layer 2 consists of an organic matrix including collagen.

The lower layers 3, 4, 5 and 6 consist of a composite matrix including collagen and hydroxylapatite.

In the context of the present invention, the quantities of collagen and hydroxylapatite are expressed in weight percent.

Preferably, the collagen is present in a lower layer in a quantity between 99 and 1%.

Alternatively, the hydroxylapatite is present in a lower layer in a quantity between 1 and 99%.

In the embodiment shown in FIG. 1, the lower layer 3 consists of a composite matrix including collagen in a quantity between 95 and 75% and hydroxylapatite in a quantity between 5 and 25%.

In the embodiment shown in FIG. 2, the lower layer 3 consists of a composite matrix including collagen in a quantity between 95 and 75% and hydroxylapatite in a quantity between 5 and 25%, while the lower layer 4 consists of a composite material including collagen in a quantity between 75 and 45% and hydroxylapatite in a quantity between 25 and 55%.

In the embodiment shown in FIG. 3, the lower layer 4 consists of a composite matrix including collagen in a quantity between 95 and 75% and hydroxylapatite in a quantity between 5 and 25%, at least a lower layer 5 consisting of a composite matrix including collagen in a quantity between 75 and 45% and hydroxylapatite in a quantity between 25 and 55% and at least a lower layer 6 consisting of a composite matrix including collagen in a quantity between 45 and 25% and hydroxylapatite in a quantity between 55 and 75%.

The multilayer structure 1 is characterized by the presence of a collagen gradient extending from the upper layer 2, in which there is 100% of collagen in the lower layer 3, in which there is a collagen quantity from 90 to 70%, until the last lower layer is reached, for example the lower layer 10, in which the collagen quantity is lower than 10%. Clearly, the hydroxylapatite quantity is complementary to the collagen quantity.

For example, the upper layer 2 has a thickness between 1 and 10 mm; preferably, from 2 to 8; still more preferably, from 3 to 5 mm.

The lower layers 3-10 can have the same or a different thickness therebetween without any restriction. The thickness of the lower layer is between 1 and 10 mm; preferably, from 2 to 8; still more preferably, 3 to 5 mm.

In the context of the present invention, by the term collagen is intended a fibrous protein of a mucopolysaccharide type which represents the greater component of the extra-cellular matrix. The collagen is recognized as the most important structural unit of the connective tissues of the human body. By the term collagen, it is actually intended a large and heterogeneous class of molecules which, besides structural functions, can have other important physiological direct or indirect functions/roles, such as cell adhesion and differentiation during the development of organs and tissues. Within the vertebrate organisms, at least 15 types of collagen with different functions are naturally present. The triple-helix molecular structure joins all the collagen types. It consists of three single chains, called α chains, each of which contains a characteristic sequence of amino acids. These three single chains are wound on one another giving rise to the typical triple-helix structure.

This conformation is stabilized by the presence of hydrogen bridges, furthermore the triple helix of the collagen is made compact and stable by a particular amino acids sequence. An amino acid every three is glycin and many of the remaining amino acids are proline or hydroxyproline. The collagen of type I represents the more abundant type of collagen existing by nature and is present in several adult connective tissues, such as the dermis, the bone, the tendon and the cornea. The collagen used in the present invention can be of type I or type II or type VI or mixtures thereof and can derive from different sources, for example by extraction from bovine, swine and horse derivation.

Alternatively, the used collagen can be of a synthetic origin, for example can be recombinant.

In the context of the present invention, by the term hydroxylapatite it is generally understood both the hydroxylapatite $Ca_{10}(PO4)_6(OH)_2$ with a high and low degree of crystallinity and the hydroxylapatite having chemical substitutions, as the inorganic/mineral component of the bone is formed by sodium, magnesium, carbonate and citrate ions.

The synthetic hydroxylapatite represents the bone substitute of largest use in surgery. However, the clinical results expressed as the quality of the neo-formed bone not always are satisfactory results. The drawback is mostly bound to the fact that the synthetic hydroxylapatite does not have the same features of the human hydroxylapatite, which from a biochemical point of view is formed with a mineralization process on collagen fibrils. For this purpose, a bio-mimetic approach for synthesizing mineral inorganic components associated with the organic components, both based on collagen or other natural or synthetic polymers, with a different chemical composition and macromolecular structure, has been widely used. The macromolecular matrixes mostly act as templates and induce the oriented deposit of the inorganic component by impeding the growth of the crystalline which remains with dimensions of 10-20 nm along the main axis (a measure completely similar to that of a natural human apatite). The interaction of HA with the collagen induces a spontaneous carbonation in the position B, which further increases the biomimetic ability and bioavailability degree of the apatite. The physical-chemical properties of the organic macromolecular components and the hydroxylapatites are influenced by the chemical interactions and the structural organization between the two components which, besides imparting geometry and morphology, establish the biomechanical properties of the device of the invention.

In a preferred embodiment of the present invention, crosslinking agents, such as glutaraldehyde, formaldehyde, ethers, bis-epoxides and hyaluronic acid have been used for imparting higher mechanical and viscoelastic properties particularly in the part formed by the collagenous layer, for example in the upper layer 2 in FIG. 1, 2 or 3.

The multilayer structure 2, shown by way of example in the enclosed FIGS. 1, 2 and 3, is obtained through an association with an upper layer 2 formed by an organic matrix including collagen and one or more lower layers formed by a composite matrix including hydroxylapatite and collagen. The upper layer 2 and a lower layer 3, for example in form of a gel, are contacted and subsequently the multilayer structure 1 is subjected to a freeze-drying or drying step.

In a preferred embodiment, the multilayer structure 1 can be associated with:

1. Some components present in the cartilaginous structure and/or the bone structure, for example through soaking or outer coating with hydrophilic biopolymers, such as hyaluronic acid and derivates (crosslinked, esters, sulphated), keratan-sulphate, chondroitinsulphate.

2. Biopolymers, for example proteoglycans and glycosaminoglycans usually contained in the extra-cellular matrix of the cartilagineous connective tissue and the bone connective respectively in an extent of 15% and 5%. Such addition allows to improve the biocompatibility and viscoelasticity properties and, at the same time, allows to reduce the compressive action of the loads.

3. Natural and synthetic polymers, such as sodium alginate, gellan, chitosan, gelatine, polylactic acid (PLLG), polyglicolyc acid (PGA), polycaprolactone (PCL), polyethylene glycol (PEG).

Advantageously, in an embodiment of the present invention, the multilayer structure can be used or associated with tissue engineering techniques which involve the use of autologous chondrocytes cultured in vitro, the use of mesenchymal cells from bone marrow precultured and expanded in vitro or pre-differentiated or completely differentiated in an osteoblast or chondroblast sense, cells from the bone marrow withdrawn from the patient in the intraoperative step to be used as such or concentrated.

Advantageously, in another embodiment of the present invention, the cartilaginous substitutes and the osteochondral substitutes can be used for surgical applications in which the reconstruction of cartilaginous and bone surfaces is required, for example in the epiphyseal laminae of the vertebral body of the spine, where the cartilaginous part consists of hyaline cartilage surrounded by a bone ring.

Advantageously, in another embodiment of the present invention, the cartilaginous substitutes and the osteochondral substitutes can be used in the femoral articular region, in the articular region of the ankle, in the maxillo-facial region (in case of reconstruction of the condyle-mandibular branch), in the osteochondral defects, in the shoulder surgery and in all kinds of orthopaedic surgery which require the formation of a new bone tissue and cartilaginous tissue for regenerating/replacing such originally existing but subsequently damaged or surgically removed tissues.

Advantageously, in another embodiment of the present invention, the novel three-dimensional composite, multilayer, bioactive and biomimetic structures can be used as cartilaginous substitutes and osteochondral substitutes. Such structures, three-dimensional matrixes or "scaffolds", surgically arranged in the cartilaginous and sub-chondral compartment subjected to a lesion/degeneration will be able to promote the regenerative processes (chondrogenesis and osteogenesis) which lead to the restoration of the anatomy, morphology and the mechanical properties of a normal osteocartilaginous tissue of the articular surfaces.

The composite matrix of the multilayer structure 1 presents an hydroxylapatite/collagen "gradient" between the different lower layers 3-10, each one containing a different quantity of collagen and nucleated hydroxylapatite independently from the thickness of each layer.

For this purpose, one can simultaneously proceed to the synthesis of the composites with a different content of apatite phase, as a function of the type of desired gradient (percentage). A direct nucleation procedure of the hydroxylapatite on the collagen fibres, which has been previously fixed, has been carried out. This nucleation reactions occur in water or SBF (synthetical physiological fluid) and in such pH conditions to allow the collagen fibres to incorporate the apatite nanonuclei.

Once the composites have been obtained, they are repeatedly washed in order to purify them from possible acid or basic reaction residues, filtered with the aid of a thin mesh sieve and spread on a surface from which it is possible to easily remove them. The single layers are then stratified inside a mould and compacted with each other. The multilayer thus obtained is dried by freeze-drying so as to obtain a spongy but resistant and compact material of a desired thickness and gradient.

As for the lower layer, that is the component which during an operation is intimately contacting the subchondral bone surface, it is preferable to obtain a structure as similar as possible to the human bone. The collagen and the hydroxylapatite and the relating mixtures are known. It is not known, on the contrary, a method for the preparation of a composite organic-ceramic three-dimensional matrix with properties similar to the human bone tissue.

An advantage of the present invention is to provide a three-dimensional substitute having a lower layer (hydroxylapatite nucleated on collagen) with the same morphological features of the human bone.

Such advantage is attained through a direct nucleation process of an apatite phase on collagen fibrils, wherein a solution of calcium salts, which promote the formation of hydroxylapatite, is reacted with similar collagenous natural polymers in an acid suspension. In the mixture of calcium salts in aqueous solution, an aqueous solution of phosphoric component, previously additioned with the acid suspension of collagen-like polymers, is dropped. The product thus obtained is subsequently subjected to freeze-drying and/or filtration and drying. The structure of the collagen-like natural polymer transfers to the molecular level those information which allow to chemically replace the hydroxylapatite, as it occurs in the human body, namely substituents, such as carbonate fractions and ionic fractions such as phosphate existing in the reaction mixture, are entered. The product obtained through such a process has identical features to those of the human bone tissue thanks to the presence of such substituents in the structure of the composite obtained. The direct nucleation acts as a mechanism of biological tendency by forming hydroxylapatite nanocrystals grown orientated parallel to the axis along the collagen fibrils, as it happens in the human body, and gives rise to an inorganic component with a low degree of crystallinity, almost amorphous and accordingly very soluble. The crystals thus formed do not grow but remain of dimensions of the order of nanometers. The nucleation of the hydroxylapatite in the collagen involves a carbonation of the inorganic phase, that is incorporation of $CO_3^{2-}$ groups in the hydroxylapatite lattice during the nucleation of the same site B in a proportion similar to that of the natural calcified bone tissue. Furthermore, the carbonation can be mostly assigned to the position B. The interaction of the hydroxylapatite with the collagen prevents the carbonation in position A by probably blocking the access to the —OH groups. This deviation from the stoichiometry surprisingly increases the similarity with the natural bone tissue and therefore not only the microstructure but also the composition of the obtained artificial tissue is exactly the same as that of the natural bone tissue. The carbonation in position B is advantageous with respect to the carbonation in position A because, as a consequence, the bioactivity and the biodegradability of the obtained artificial bone tissue remarkably increase, which are essential features for the calcification as they allow a continuous dynamic exchange between the physiological fluid and the cell which uses the ions for the bone formation.

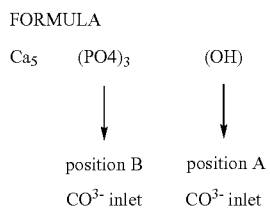

The present invention uses an approach of biological tendency for synthesizing hydroxylapatite nanocrystals on self-assembling collagen fibrils similar to the nanocrystals of natural bones, by exploiting the ability of the negatively charged collagen carboxyl groups of binding calcium ions of the hydroxylapatite; following this approach, it has been successfully proved that the biological systems store and process information at a molecular level. For this reason, the collagen molecules of type I without telopeptides and free of glucosylated regions, capable of self-aggregating in fibrils without crosslinking agents, have been used as starting materials.

Collagen Preparation

The collagen of type I has been found on the market as a standard product. After the purification process, the collagen of type I is dissolved in an estimated volume of acetic acid until a homogeneous suspension is obtained (1% collagen).

In a preferred embodiment, calcium salts in aqueous solution or SBF (synthetic body fluid) are used, which promote the hydroxylapatite formation, preferably selected from the group including calcium hydroxide, calcium nitrate, calcium acetate, calcium sulphate, calcium carbonate. More preferably, calcium hydroxide is used. Furthermore, an acid suspension of collagen-like natural polymer is used, obtained by treatment of animal collagen extracted from horse tendon, mouse tail, kangaroo tail or collagen-like synthetic polymer or chemically crosslinked gelatines. Moreover, the phosphate component used has been selected among phosphoric acid in acqueous solution or SBF or a calcium, ammonium, sodium, potassium and magnesium salt in acqueous solution with a phosphate anion $PO_4^{(3-)}$, mono-hydrogen phosphate $HPO_4^{(2-)}$ or dihydrogen phosphate $H_2PO_4^{(-)}$. More preferably, phosphoric acid $H_3PO_4$ is used. The calcium salts used by the present invention are in the range between 1 and 4 gm./l, the phosphate component is in the range between 2 gm./l and 4 gm./l. More preferably, the calcium salts used in the present invention are in the range between 2 and 3 gm./l, the phosphate component is the range between 3 and 4 gm./l.

The direct nucleation step occurs with a pH preferably between 9 and 12, more preferably between 9-11 (at the end of the reaction the pH must be between 7 and 8.5 or more preferably between 7 and 7.5) and at a temperature preferably between 25 to 45° C., more preferably between 35 and 40° C.

In a preferred embodiment, in an aqueous or SBF solution of $Ca(OH)_2$ (147 gm. of $Ca(OH)_2$ in 300 cc of $H_2O$) a phosphoric acid solution (1.17 gm. Of $H_3PO_4$ in 200 cc of $H_2O$) and 50 gm. of collagen in acetic acid were dropped. The pH during the process was between 7-10, the temperature was maintained around 25° C., the dropping time of the phosphoric acid solution in the mixture of calcium salts in acqueous solution and acid suspension of collagen was maintained between 15 and 60 minutes and therefore the dropping rate was preferably between 0.0133 l/minute and 0.0033 l/minute, more preferably between 0.0100 and 0.0060 l/min. The obtained products, coded HA/Col nuc. col. were subsequently subjected to a freeze-drying or drying step.

Therefore, the composites have been characterized by crystal analysis with a x-ray diffractometer (Rigaku Miniflex); for analysing the orientation, some diffraction graphs have been photographically recorded with a sample-film distance of 70 mm by using a flat chamber (always with Cu-Kα radiation).

The thermogravimetric analysis has been carried out (Polymer STA 1660) by using an alumina crucible in air and using a heating rate of 10° C./min.

Analysis of the Composites

The composites prepared according to the method of the present invention by direct nucleation of hydroxylapatite in the collagen fibrils had a hydroxylapatite/collagen nominal composition from 80/20 to 10/90 as a mass. However, by thermogravimetric analysis it has been found that the actual composition was respectively 70/30 and 10/90. This discrepancy is due to the reaction yield which does not reach 100%. The water content in the compound is very similar to that of pure collagen (10%). This analysis has been successfully used in order to obtain information about the modifications of the structural relations between collagen fibrils and inorganic phase as a function of the mineral content. Previously, such analysis has been carried out on the flexor tendon of the turkey foot which is used as a pattern in the calcification process.

In fact, the TG-DTG graphs seem modified with respect to those of the hydroxylapatite/collagen compounds, which show, an interaction of the inorganic phase with the collagen fibres. This kind of interaction can be compared to the calcification process which naturally occurs. The comparison is carried out with a TG-DTG graph relating to a turkey calcified tendon, used as a bone theoretical pattern. The close similitude is apparent because in both cases the DTG peak at 450-500° C. tends to disappear by forming an "enlarged shoulder".

It can be supposed that, when a direct nucleation of hydroxylapatite on collagen is carried out, the composite behaves as a naturally calcified tissue.

The XRD crystallogram shows a typical graph of hydroxylapatite with a very low crystallinity, the sizes of the estimated crystals along the axis is about 12-15 nm. The nucleation occurs according to the typical process of the natural bone, in which the nanodimension of the crystals is responsible of the extension of the reflection in the graph. Furthermore, as the reaction has been carried out at about 25° C., one is widely within the limits for forming nanocrystals of monocristalline hydroxylapatite. Such nanocrystals grow within the collagen fibres with their c axis preferably oriented parallel to the orientation direction of the fibres. In fact, the diffraction graph of the wide X-ray angle is obtained from a sample consisting of some calcified fibrils.

The TEM micrograph shows nano-nuclei formed within the collagen fibrils which grow parallel to the fibrils. Such analytic techniques have pointed out strong interactions between the two collagen and hydroxylapatite components and a complete analogy of the composite with the calcified natural tissue.

Furthermore, the analysis under the optical microscope shows the different crystalline morphology of the hydroxylapatite/collagen composite obtained by direct nucleation and subsequently freeze-dried from the one air dried. The freeze-dried composites show a three-dimensional network characterized by a very large pore distribution similar to that of the cotton and the wool. When the sample is dried on an air filter, on the contrary, a two-dimensional network is formed and the structure looks like a gauze fill.

The artificial bone tissue according to the present invention can be obtained with different quantities of hydroxylapatite/collagen and various formulations and is suitable to several clinical applications. Such artificial bone tissue can be used as a constituent of the lower HA-collagen layer/s of the cartilaginous/osteo-cartilaginous substitute of the present invention and also as a prosthetic material, for replacing or filling the bone, as a reconstructive membrane or haemostatic tissue in orthopedics, odontotherapy, maxillofacial surgery.

Advantageously, the substitutes above mentioned can be used as an osteochondral substitute for cartilaginous defects of 3 and 4 Outerbridge degree or for cartilaginous defects of deep 4 Outerbridge degree.

Experimental Part

Figure 4:
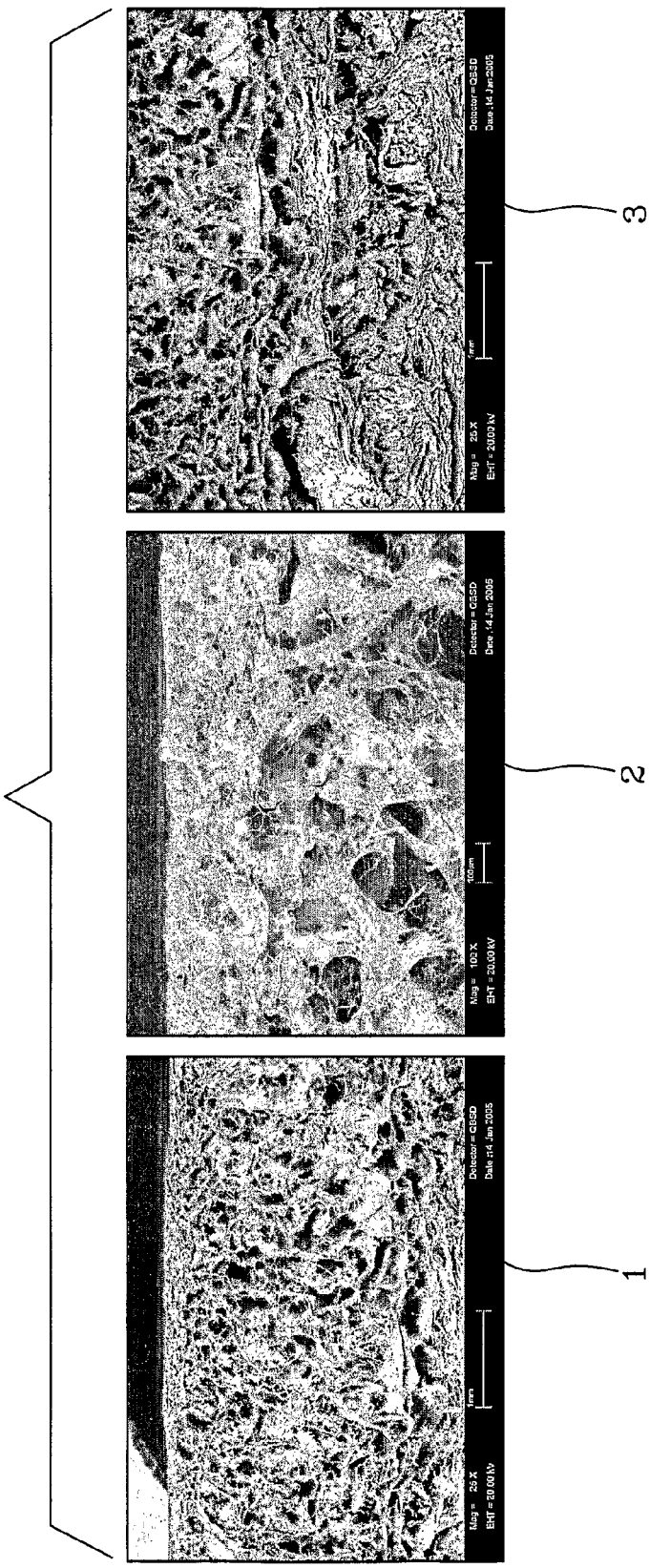
FIG. 4 shows the collagenous structure of the prototype A' without addition of any crosslinker in the preparation step. Image (1) shows a detail of the porous structure of the collagenous layer; image (2) shows an enlargement of the porous structure of the collagenous layer; and image (3) shows an interface between collagenous layer—gradient HA/collagen.
Figure 5:
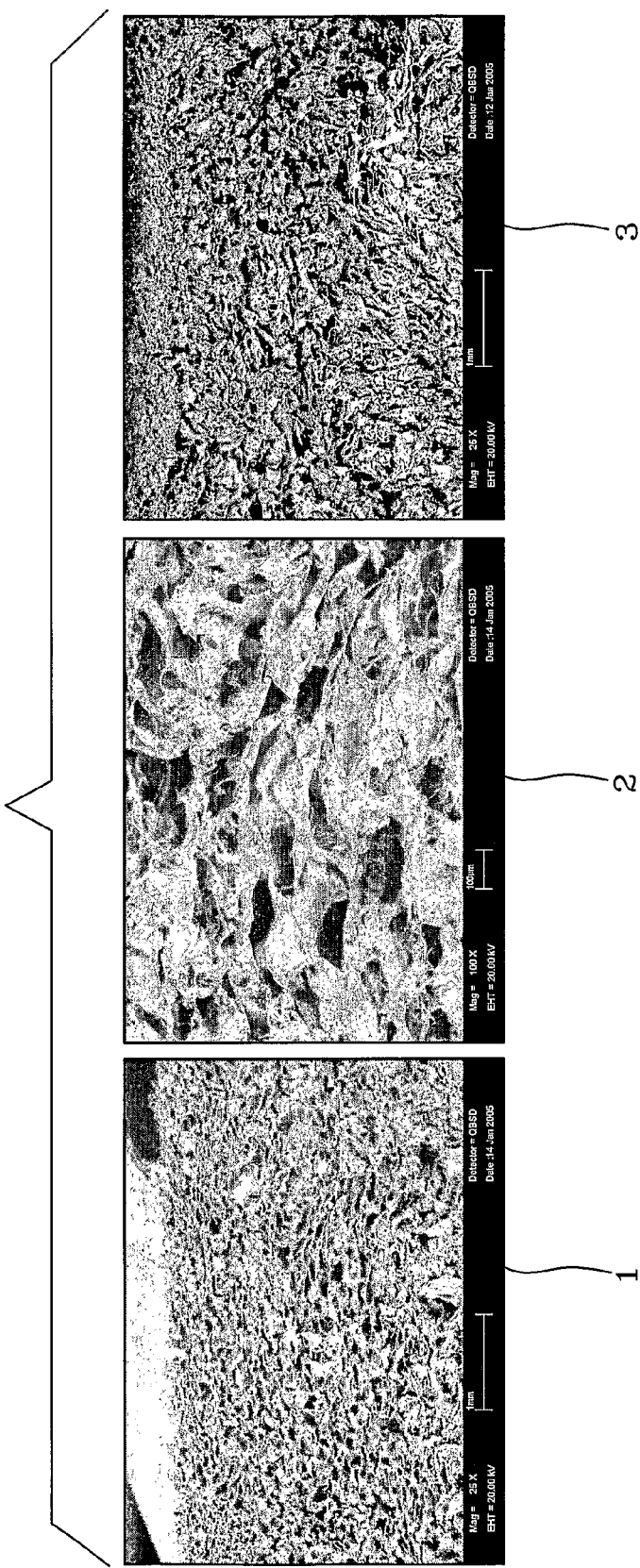
FIG. 5 shows the porosity of a collagenous layer B' with the addition of hyaluronic acid in the preparation step. Image (1) shows a detail of the porous structure of the collagenous layer; image (2) shows an enlargement of the porous structure of the collagenous layer; and image (3) shows an interface between collagenous layer—gradient HA/collagen.
Figure 6:
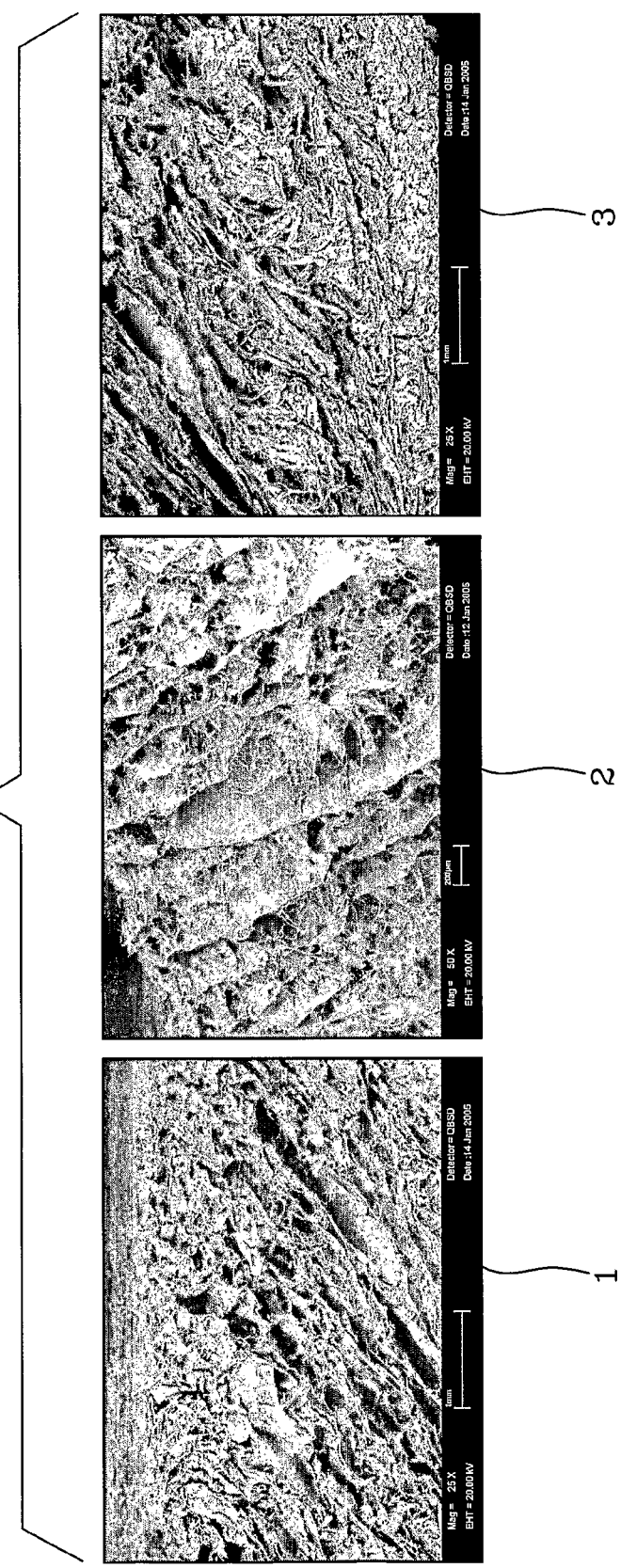
FIG. 6 shows the porous structure of a sample C' subjected to crosslinking through addition of 1,4-butanediol-diglycidyl ether (BDDGE). Image (1) shows a detail of the porous structure of collagen oriented in a vertical direction; image (2) shows an enlargement of the porous structure of collagen oriented in a vertical direction; and image (3) shows a detail of the interface between collagenous layer—gradient HA/collagen.
Figure 9:
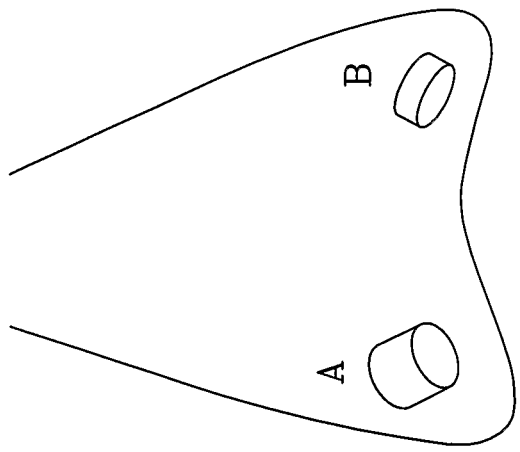
FIG. 9 shows a diagrammatic illustration of the condyle of a horse.
Figure 8:
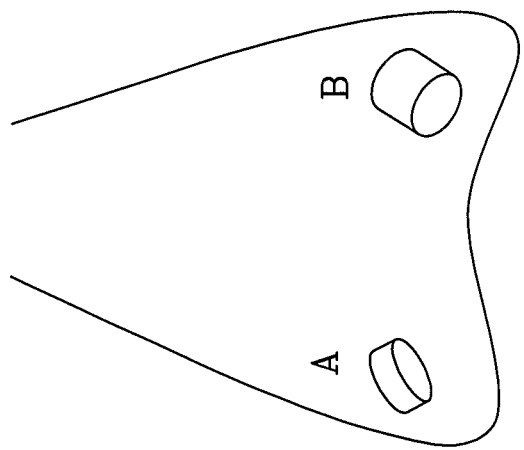
FIG. 8 shows a diagrammatic illustration of the condyle of a horse.
Figure 10:
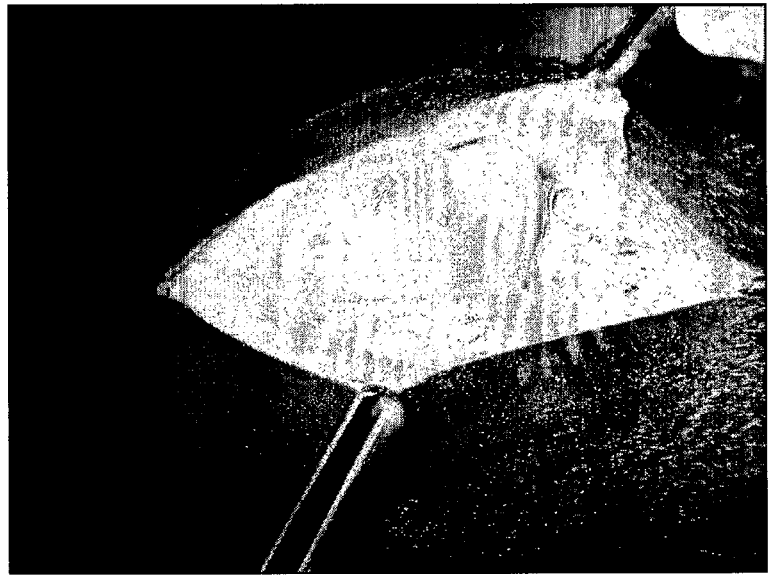
FIG. 10 shows an open and incised anatomic region.
Figure 11:
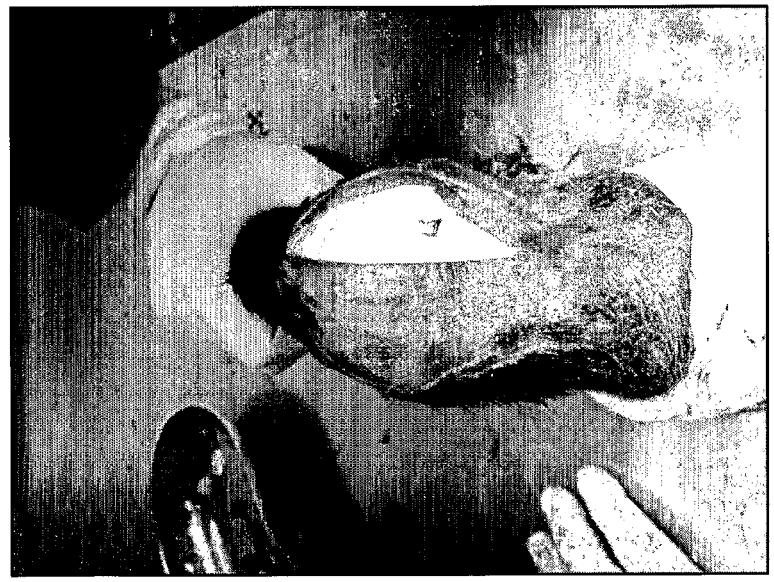
FIG. 11 shows the exposure of the condyle surfaces.
Figure 13:
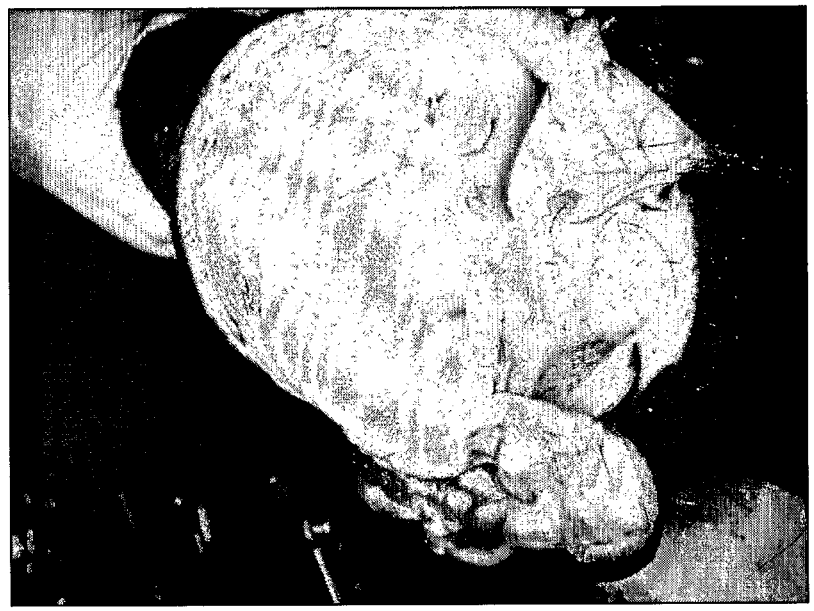
FIG. 13 shows an example of the positioning of the device.
Figure 12:
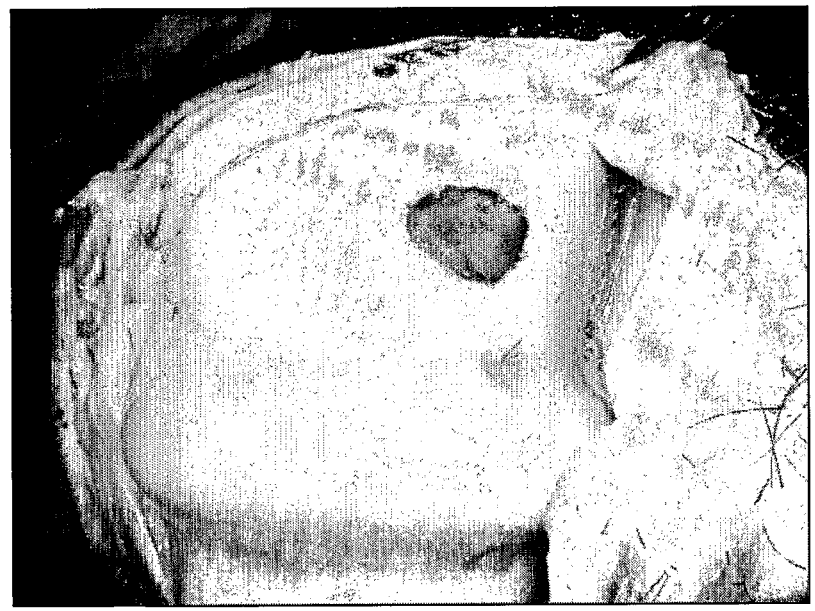
FIG. 12 shows a lesion on the cartilaginous surface with exposure of the sub-chondral bone.
Figure 14:
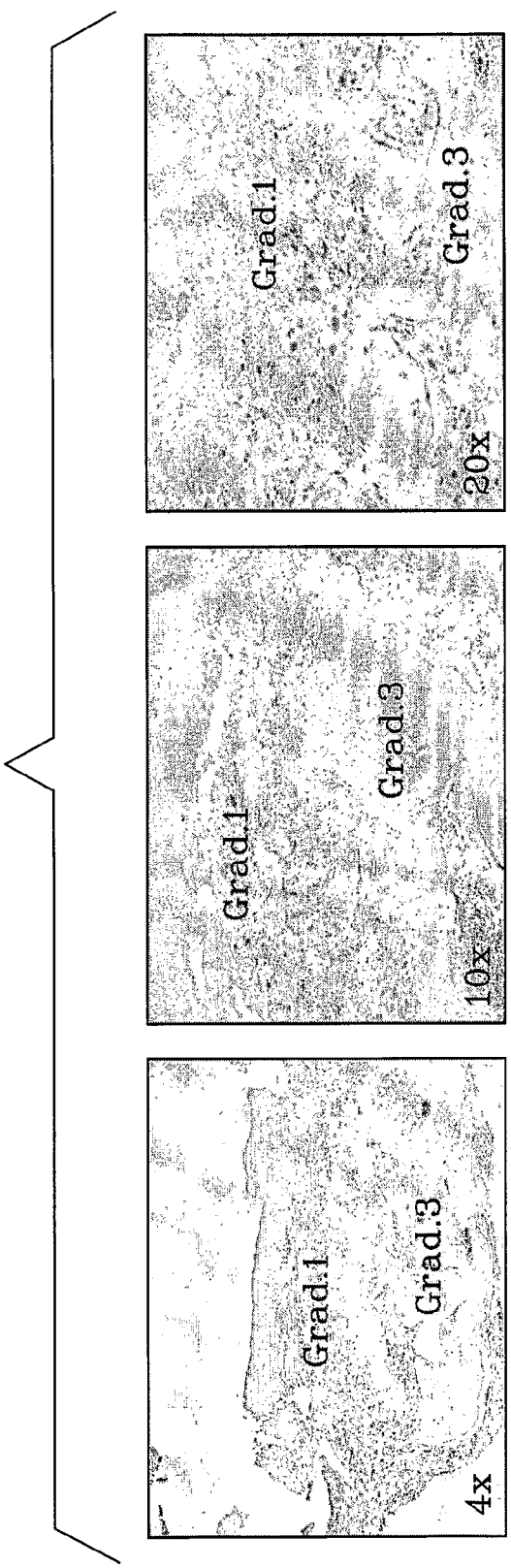
FIG. 14 shows a histological analysis after 8 weeks (hematoxylin/eosin staining)
Figure 15:
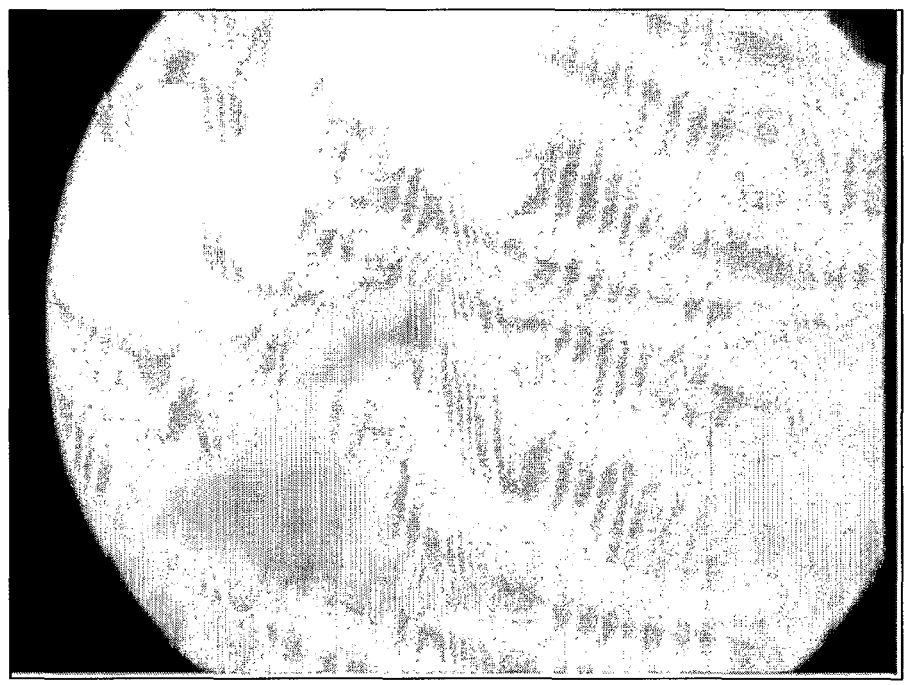
FIG. 15 shows an arthroscopic "$2^{nd}$ look"
Figure 16:
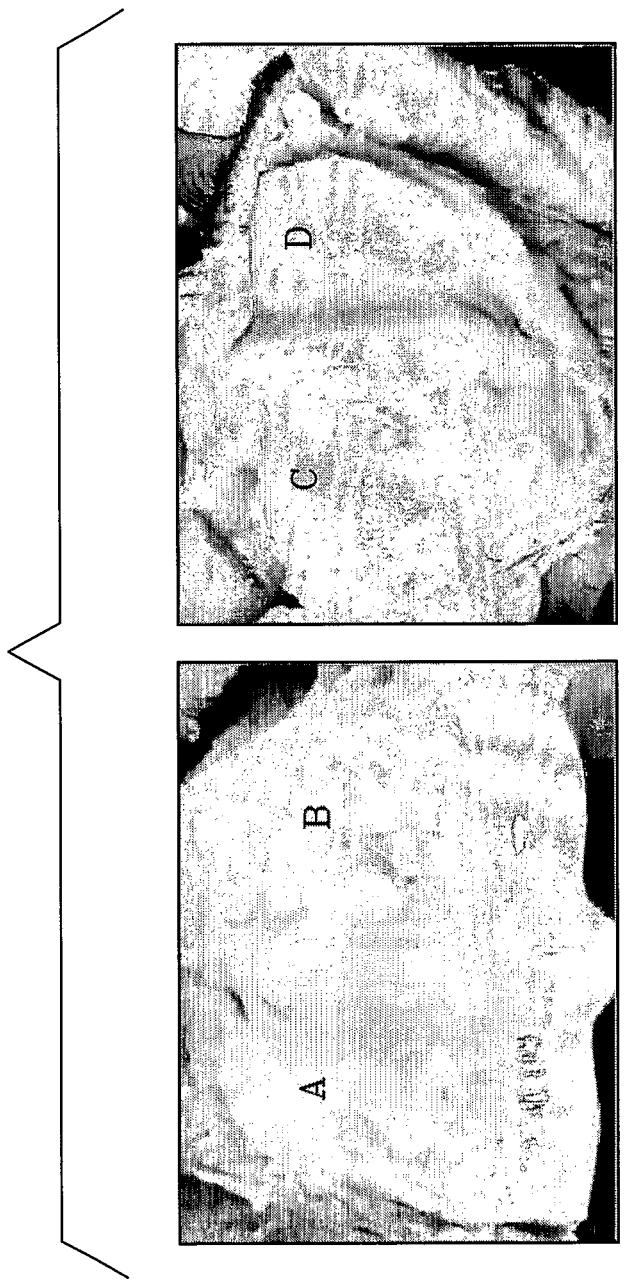
FIG. 16 shows a "$2^{nd}$ look" on the animal no. 1.
Figure 17B:
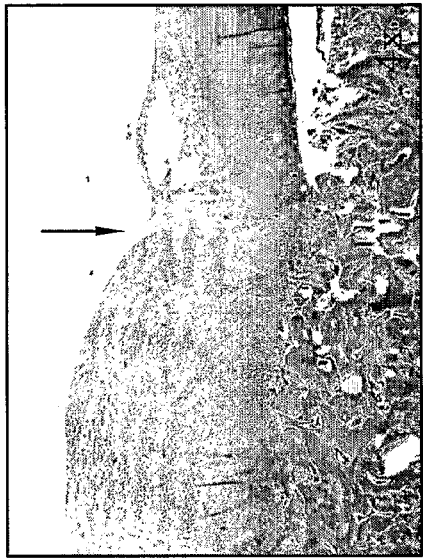
FIG. 17 (A-H) shows a histological analysis with a staining of toluidine blue in different enlargements of the chondral implant (animal 1).
Figure 17D:
Figure 17A:
Figure 17C:
Figure 17F:
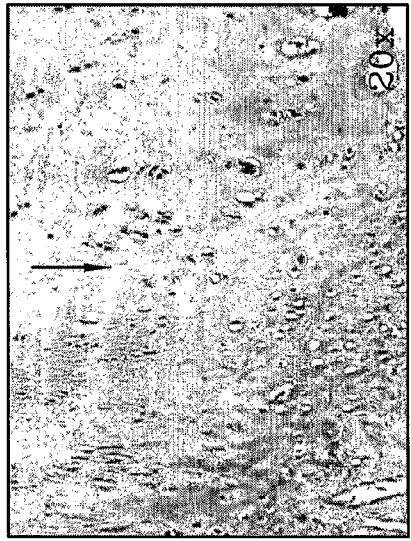
Figure 17H:
Figure 17E:
Figure 17G:

The experimental part will be now described with reference to the enclosed figures and images, which show some not limiting embodiment examples, wherein:

FIG. 4 shows the collagenous structure of the prototype A' without addition of any crosslinker in the preparation step. The prototype A' is just a sample without addition of any crosslinker in the preparation step. In FIG. 4 it is shown: by (1) a particular of the porous structure of the collagenous layer, by (2) a high enlargement of the porous structure of the collagenous layer, by (3) an interface collagenous layer-HA gradient/collagen;

FIG. 5 shows the porosity of a collagenous layer B' with the addition of hyaluronic acid in the preparation step. The prototype B' is a sample with the addition of hyaluronic acid in the preparation step. In FIG. 5 it is shown: by (1) a particular of the porous structure of the collagenous layer, by (2) a high enlargement of the porous structure of the collagenous layer, by (3) an interface collagen surface-HA gradient/collagen;

FIG. 6 shows the porous structure of a sample C' subjected to crosslinking through addition of 1,4-butanediol-diglycidyl ether (BDDGE). In FIG. 6 it is shown: by (1) a particular of the porous structure with orientation in a vertical direction, by (2) a particular with a high enlargement of the porous structure with an orientation in the vertical direction of the walls of the pores, by (3) a detail of the interface HA gradient/collagen;

FIG. 7 shows the porous collagenous structure of the prototype D' subjected to crosslinking through glutaraldehyde vapours treatment. In FIG. 7 it is shown: by (1) a particular with high enlargement of the porous structure of the collagenous layer, by (2) an interface collagenous layer-HA gradient/collagen;

FIG. 8 shows a diagrammatic illustration of the right condyle of a horse. In FIG. 8 it is shown: by (A) a chondral lateral lesion+microabrasions with a device positioning with 2 gradients (cartilaginous substitute, configuration I), by (B) an osteochondral medial lesion+bleeding with a scaffold positioning with 3 gradients (osteo-cartilaginous substitute, configuration II);

FIG. 9 shows a diagrammatic illustration of the left condyle of a horse. In FIG. 9 it is shown: by (C) an osteochondral medial lesion+bleeding with a scaffold positioning with 3 gradients (osteo-cartilaginous substitute); by (D) a chondral lateral lesion+microabrasions with a device positioning with 2 gradients (cartilaginous substitute);

FIG. 10 shows an open and incised anatomic region;

FIG. 11 shows the exposure of the condyle surfaces;

FIG. 12 shows a lesion on the cartilaginous surface with exposure of the sub-chondral bone;

FIG. 13 shows an example of the positioning of the device;

FIG. 14 shows a histological analysis after 8 weeks (hematoxylin/eosin staining). FIG. 14 shows the presence, of fibrous tissue in correspondence with the gradient 1 of collagen alone. In the deepest zone, in correspondence with the gradient 3 with a prevalent hydroxylapatite component, the presence of a bone neo-formation is noted;

FIG. 15 shows an arthroscopic "$2^{nd}$ look";

FIG. 16 shows a "$2^{nd}$ look" on the animal no. 1. FIG. 16 shows a regrowth of the connective tissue on the lateral chondral lesions A and D and on the medial osteochondral lesions B and C;

FIG. 17 (A-H) shows a histological analysis with a staining of toluidine blue in different enlargements of the chondral implant (animal 1).

The chondral or osteochondral substitute (scaffold) of the present invention has been chemically modified so as to render all the general structure more elastic and more hydrophilic, therefore less subjected to delamination at the interface between the lower surface $2b$ of the upper layer $2$ and the upper surface $3a$ of the lower layer $3$ during the handling carried out by the operator.

The delamination phenomenon of the layers is a drawback which occurs when the substitute, once prepared, is hydrated. The delamination represents a problem which has to be necessarily overcome.

A multilayer structure $1$ presents an upper layer $2$ consisting of collagen of type I and a lower layer $3$ consisting of hydroxylapatite/collagen type I (40%-60%).

Another multilayer structure $1$ presents an upper layer $2$ consisting of collagen of type I and a lower layer $3$ consisting of hydroxylapatite/collagen type I (40%-60%) and a lower layer $4$ consisting of hydroxylapatite/collagen (70%-30%).

For each of the two multilayer configurations, 4 prototypes have been prepared, whose chemical and geometrical features after the freeze-drying are reported in FIGS. 1 and 2.

Each prototype has been freeze-dried (when brought to the temperature of $-40°$ C., once completely frozen, it is subjected to a vacuum of about $7 \cdot 10^{-2}$ Pirani (1 Pirani=$1 \cdot 10^{-3}$ mBar), therefore heated up to $30°$ C. by maintaining the vacuum degree) in a Petri dish and subdivided in 4 portions of 12 cm$^2$ each with the use of a sharp knife. All the prototypes have been packaged in single packagings and sterilized by γ-radiation at 25 kGy.

A sterile portion has been subjected to the following tests:
dry handling;
wettability;
optical microscopy;
SEM structural analysis.

A sterile portion has been subjected to in vitro and in vivo tests and in vivo handling tests on sheep and on fetlock cartilage from a horse cadaver. Finally, an aliquot for carrying out further tests and chemical analysis has been kept.

The samples B and C result, for their intended purpose, the more suitable both for their good elasticity properties and the high hydrophilicty degree:
the elastic flow to the handling is a property which promotes the use thereof
the hydrophilicty is a very important parameter because facilitates the migration, within the scaffold, of the mesenchymal-stem cells coming from the bone marrow; this, accordingly, allows, within the scaffold, the cell differentiation and the regeneration of the tissues to be repaired.

At a dry state a good compactness of the prototypes is observed, a greater elasticity and compression flow for the prototypes B and C for both the I and II versions is apparent. For the prototype D, which presents a yellow-tending staining probably due to the glutaraldehyde vapor treatment, a rigidity is noted.

The wettability tests have been carried out in water, by dipping, handling and rehydrating each single scaffold portion and have observing it up to a week. For all the versions, a stability up to two days was observed. The prototypes B and C showed a fast hydration ability and a higher swelling than the prototypes A and D. The version D showed a greater rigidity.

On the third examination day, the stability sensibly decreased for the prototype A with a fibre loss and a partial delamination at the gradient boundary, while a slight fibre loss was visible in the prototype B and C. The version D maintained intact the initial geometry when subjected to handling.

On the seventh day, the almost total delamination of the layers was noted in the prototype A, while B and C showed a loss of collagen fibres with a partial delamination. The prototype D maintained the initial geometry.

Optical Microscopy and ESEM

The optical microscope observations at 12× have been carried out on 2 mm sagittal sections of each configuration. The ESEM images have been acquired at 25 and 100×.

FIG. 4 shows a series of images of a scanning electron microscopy alone, relating to all the prototypes of the configuration I of the scaffold.

In FIG. 4, the collagenous structure of the prototype A' shows a rather regular porosity (1), but with a greater enlargement the walls of the pores seem more indented (2). The interface collagen-hydroxylapatite gradient/collagen 40/60 is apparent (3).

FIG. 5 shows the porosity of the collagenous layer of the prototype B', which is regular and rather compact relative to the prototype A'. This compactness is probably to be intended as an artifact due, on a greater extent, to the blade action during the cut of the scaffold rather than to an action of the hyaluronic acid on the structure (1). With a greater enlargement, the conservation of the pore regularity is noted, with a similar conservation of the surface regularity of the internal walls (2). Particular orientations of the pores are not visible. On the contrary, a greater uniformity and compactness of the single structures at the interface collagen-HA gradient/collagen (3) seems to be visible.

In FIG. 6 the observation of the prototype C is reported. The interesting element appearing from the observations of the prototype C is the porous structure of the collagen oriented in a vertical direction (1). Wide lamellar structures which could promote and orientate the migration and the differentiation in a chondrocytal direction of the parent cells or the chondrocytes possibly loaded on the scaffold (2) are apparent. Also in this case, the interfaces collagen-HA gradient/collagen seem well connected (3).

In FIG. 7 the observation of the collagenous porous structure of the prototype D' is reported with a high enlargement. From FIG. 7, a greater compactness relative to all other prototypes (1) is observed. The porosity is of definitely lower dimensions than the structures previously analyzed. Also in this case the interface between the two layers is much more compact by imparting a reduced height of the scaffold (2).

The addition of plasticizers or crosslinking agents during the preparative step of the scaffold is able to impart a greater stability to their structure.

The stability requirement for a collagen-based scaffold, which can be engineered or not, represents the determining element.

In this development step, hyaluronic acid with a medium molecular weight, a crosslinking agent belonging to the family of the bis-epoxides (diglycidyl ether) and glutaraldehyde vapours or its derivates have been used as agent capable of increasing the hydrophilic and plastic properties of the construct.

The preliminary results attained through "handling" tests and ESEM observations show that the best mode for the collagen stabilization is obtained by crosslinking with 1,4-butanediol-diglycidyl ether (BDDGE). In the following, an experimental part relating to in vivo and in vitro tests, carried out for checking the behaviour of the osteochondral scaffold of the present invention, is reported.

The aim of the experiments was to check the in vivo behaviour of a configuration of chondral and osteochondral scaffold with a configuration with two (cartilaginous substitute) and three gradients (osteocartilaginous substitute) respectively, subjected to a crosslinking with BDDGE (1,4-butanediol-diglycidyl ether) in the preparation step.

The selected animal models were:

1) implant on a nude mouse of the three gradients configuration of the scaffold (osteochondral scaffold) loaded with sheep stromal parent cells (BMSC) derived from bone marrow;

2) implant of the two configurations of the scaffold following to a cartilaginous and osteo-cartilaginous lesion on the horse femoral condyle.

1) Implant of the BMSC-loaded Scaffold.

The aim of the present study was to check the bone and cartilaginous neo-formation of the three-phase scaffold or with a configuration II (gradient 1 collagen type I, gradient 2 collagen type I/hydroxylapatite ratio 70%/30%, gradient 3 collagen type I/hydroxylapatite ratio 30%/70%) loaded with sheep stromal parent cells (BMSC) coming from a withdrawal of medullary blood. The scaffold has been implanted on an intramuscular site (extra-skeletal or heterotopic site) in an immune-depressed nude mouse for the purpose of checking the tissue differentiation within the gradients of the osteochondral scaffold.

1) Cell differentiation in a bone sense within the gradient 3;

2) cell differentiation in a cartilaginous sense in the gradient 1 consisting of collagen alone.

2) Implant of the scaffold following to a cartilaginous and osteo-cartilaginous lesion on a horse.

The aim of the present in vivo study was to check in no. 2 animals, after a cartilaginous and osteocartilaginous lesion in the distal epiphisys of the third metacarpal (fetlock) of a horse, the behaviour of the configurations with 2 and 3 gradients of the scaffold prepared with a nucleation process of hydroxylapatite nano-particles on collagen fibres subjected to a crosslinking process by BDDGE (1,4-butanediol-diglycidyl ether). The two forms of the scaffold were represented by: configuration I or two-phase scaffold (2 gradients) whose intended use is a cartilaginous substitute scaffold for the treatment of chondral lesions and configuration II or three-phase scaffold (3 gradients) whose intended use is an osteo-cartilaginous substitute scaffold for the treatment of severe degree or deep osteochondral lesions.

The following evaluations have been carried out:

1) stability of the scaffold (fixing, permanence in the implant seat) through arthroscopic control after three months;

2) restoring of the cartilaginous mantle previously removed, radiological and histological analysis of the biopsies taken at a distance of at least six months from the implant.

Surgical Procedure.

After a period of 7 days of acclimatization and a pre-operating pharmacological treatment, the 2 animals were subjected to a radiographic control of the joints for excluding the presence of any pathological alterations. The horses are maintained without food the 12 hours before the operation.

At the time of the surgery, the animals were anaesthetized with a solution composed of 5% guaiacolglyceric glucose containing 3 gm. of sodium thiopental. The keeping of the anaesthesia was granted though allotane in an oxygen mixture.

After positioning of the animals in a lateral decubitus in both the forelimbs, the circulation was blocked with a vascular emptying of the carpus. In sterile conditions, a miniarthrotomy was performed on the dorsal face of the fetlock in correspondence with the distal end of the metacarpal III° (FIG. 10), laterally and in an upper position with respect to the tendon of the dorsal extensor muscle of the digit. On the decubitus fetlock, the miniarthrotomy was performed medial to the mentioned tendon.

By placing the flexing fetlock the distal part of the lateral condyle (upper fetlock) and the medial condyle (decubitus fetlock) was exposed (FIG. 11). By means of a proper power-driven milling cutter a circular defect of the articular cartilage was carried out, with dimensions of 1.0 cm$^2$ until the complete exposure of the sub-chondral bone for a deep of about 5 mm in case of chondral lesion and 8-10 mm in case of osteo-chondral lesion. In both cases, microabrasions (FIG. 12) were performed. The dimensions of such lesions ensure the scaffolds housing in their configurations.

The scaffolds were placed within the holes and maintained in the seat for a few seconds through digital pression until a swelling was reached, which ensured its fixing to the walls of the lesions (FIG. 13).

At the end of the operation, the sutures of the surgical incisions were carried out by levels in the following way: separated-spot suture of the articular capsule with polyglycolic acid No. 0, continuous suture of the digital fascia with polyglycolic acid No. 00 and separated-spot suture of the dermis with nylon No. 0.

The procedure was then repeated in an identical way on the remaining metacarpal portions after having inverted the decubitus of the horse. In total, for each animal 4 miniarthrotomies and the implant of 4 scaffolds (two chondral scaffolds, configuration I, and two osteochondral scaffolds, configuration II) were then carried out. At the end of the operation, semi-rigid bandages from the hoof to the carpus were applied. The surgical and treatment pattern for both the animals is reported below.

In FIG. 8 a left condyle is reported:

A. Chondral lateral lesion+microabrasions with positioning of 2 gradients device (cartilaginous substitute, configuration I).

B. Osteochondral medial lesion+bleeding with positioning of 3 gradients scaffold (osteo-cartilaginous substitute, configuration II).

In FIG. 9, a right condyle is reported:

C. Osteochondral medial lesion+bleeding with positioning of 3 gradients scaffold (osteo-cartilaginous substitute).

D. Chondral lateral lesion+microabrasions with positioning of 2 gradients device (cartilaginous substitute).

At the end of the surgical operation, the animals were subjected to an antibiotic and anti-inflammatory pharmacological treatment. At the awakening, the normal deambulation with immediate load was allowed.

Results

1) Implant of the Scaffold Loaded with BMSC

Histological Analysis after 8 Weeks

The animals were sacrificed after 8 weeks and the implant site was accurately removed and processed for hematoxylin/eosin staining. The microscopic observations pointed out a bone neo-formation within the gradient with a prevalent hydroxylapatite component (gradient 3), while no bone exceeding in the collagenous portion (gradient 1) intended for a cartilaginous neo-formation (FIG. 14) was observed.

The data show how the hydroxylapatite can play a "priming" function, namely it is able to activate the cell differentiation process, in a bone sense, in the deepest layer, whereas within the more superficial layers the collagenous composition of the scaffold guides the cell differentiation in a cartilaginous sense.

2) Implant of the Scaffold Following to a Cartilaginous and Osteo-Cartilaginous Lesion on a Horse 2$^{nd}$ Arthroscopic Look The arthroscopic check was carried out after 3 months from the first operation date. The images pointed out, within the chondral and osteochondral lesion site of both the forelimbs, a neo-formation of connective tissue which resulted of a good consistency at the sight, however it was not distinguishable from a fibrous tissue. In some zones of the operation surface, scaffold traces were apparent. From the arthroscopic observations carried out on the animal no. 2 in correspondence with the lateral lesion, no reaction of an inflammatory type, nor a displacement of the device were apparent (FIG. 15).

Macroscopic Evaluations at the Euthanasia.

The animals were killed in an average interval of 214±11 days. The animals were sacrificed through intravenous injection of a Tanax solution, by previous administration of general anaesthesia.

For each animal, both the limbs were removed 20 cm in a proximal portion relative to the joint (fetlock) where the surgical operations were carried out.

Both the condyles of the joints were carefully exposed by preserving the operation surface in the medial and lateral zones. The neo-formed tissue in the implant zones of the scaffolds was macroscopically evaluated. On the implant areas in the medial zones (osteocartilaginous scaffold), a good neo-formation of bright connective tissue, with healing of the tissue until the healthy cartilage level, was apparent. On the articular cartilage surface, corresponding to the cartilaginous implant (lateral condyles), the same situation of the medial condyle with a formation of connective tissue until the complete rearrangement of the hole was observed (FIG. 16).

In FIG. 14 the histological analysis after 8 weeks (hematoxylin/eosin staining) is reported. The presence of fibrous tissue was found in correspondence with the gradient 1 of collagen alone. In the deepest part, in correspondence with the gradient 3 with a prevalent hydroxylapatite component, the presence of a bone neo-formation is noted.

FIG. 15 relates to the arthroscopic "2$^{nd}$ look".

FIG. 16 relates to the "2$^{nd}$ look" of the animal no. 1. The regrowth of the connective tissue on the lateral chondral lesions A and D and on the osteochondral medial lesions B and C.

FIG. 17 relates to the histological analysis with a toluidine blue staining with different enlargements of the chondral implant (animal 1).

The reported histological images (FIGS. 17 A to H) relate to the animal no. 1, lateral lesion corresponding to the chondral implant.

The operation zones were carefully removed, by also collecting a health cartilage portion surrounding the lesion.

Each collection was divided in two parts and the cutting at the microtome was performed from the centre to the periphery and stained with toluidine blue for the microscopic observations.

The microscopic observations pointed out a high bone formation in the lower and deepest part of the chondral scaffold. The surface collagenous layer was colonized by a fibrocartilaginous tissue distinguishable from the healthy cartilaginous tissue and the presence of exceeding bone tissue within it was not found.

The analysed sample, of about 1 cm$^3$, has been collected at the implant level and includes the surrounding area of articular cartilage. The sample has been decalcified and included in paraffin. The sections have been cut at a thickness of about 10 μm and stained with toluidine blue.

The photographs concern the two ends of the implant, namely the zones of interest at the healthy articular cartilage-implant interface.

There may be noted the residual zones of articular cartilage bordering upon a new formed tissue from the apparent appearance of fibrocartilages.

The implant itself seems superficially formed with fibrocartilage and fibrous connective tissue without any trace of tissue morphologically referable to an articular and deep cartilage of bone tissue.

The neo-formed bone tissue (visible in A and B) seems to be well integrated with the surrounding bone, the cartilaginous tissue presents an apparent demarcation line (arrow) which marks the passage from the pre-existing articular cartilage to the neo-formed fibrocartilage.

The invention claimed is:

1. Cartilaginous or osteochondral substitute comprising a multilayer structure including:
    an upper layer consisting of crosslinked collagen fibers; and
    one or more lower layers consisting of crosslinked collagen fibers and crystals of Mg- and CO$_3$-substituted hydroxylapatite wherein said crystals are nucleated between and parallel to the crosslinked collagen fibers and have dimensions ranging from 10 to 20 nm;
wherein said upper layer and said one or more lower layers are in direct contact with each other, and wherein said multilayer structure comprises a collagen-hydroxyapatite gradient characterized by a quantity of crosslinked collagen fibers of 100% in the upper layer and ranging down to between 99% and 1% in at least one lower layer, and wherein the gradient further comprises said crosslinked collagen fibers oriented in a vertical direction.

2. The cartilaginous or osteochondral substitute according to claim 1, wherein the multilayer structure is a scaffold for in situ attachment and differentiation of mesenchymal cells.

3. The cartilaginous or osteochondral substitute according to claim 1, wherein the multilayer structure is loaded ex-vivo with a concentrate from medullary blood or with a platelet concentrate or with growth factors or factors capable of promoting trophism and cell differentiation.

4. The cartilaginous or osteochondral substitute according to claim 1, wherein the multilayer structure is loaded ex-vivo with mesenchymal cells which are undifferentiated or maintained in a culture for a time period required for multiplication and/or differentiation in parent cells of osteoblasts and chondrocytes.

5. The cartilaginous or osteochondral substitute according to claim 1, wherein the multilayer structure is loaded with pharmacologically active substances selected from the group consisting of: anti-inflammatory corticosteroids, FANS, immunosuppressors, antibiotics, antiblastics, antiproliferatives and antivirals.

6. The cartilaginous or osteochondral substitute according to claim 1, wherein the crosslinked collagen fibres are crosslinked with hyaluronic acid or a salt thereof or a derivative thereof.

7. The cartilaginous or osteochondral substitute according to claim 1, wherein the crosslinked collagen fibres are crosslinked with BDDGE or a derivative thereof.

8. The cartilaginous or osteochondral substitute according to claim 1, wherein the crosslinked collagen fibres are crosslinked with at least one crosslinker selected from the group consisting of: glutaraldehyde or a derivative thereof, and bis-epoxides.

9. The cartilaginous or osteochondral substitute according to claim 1, in a freeze-dried or dried form.

10. The cartilaginous or osteochondral substitute according to claim 1, in a sterilized form.

11. Method for treating articular cartilaginous defects or osteochondral defects or for the neo-formation of a cartilaginous tissue and/or a subchondral bone tissue, which comprises implanting a cartilaginous or osteochondral substitute according to claim 1.

12. The cartilaginous or osteochondral substitute according to claim 1, wherein at least one lower layer consists of crosslinked collagen fibers in a weight quantity between 75 and 45% and hydroxylapatite in a weight quantity between 25 and 55%.

13. The cartilaginous or osteochondral substitute according to claim 1, wherein at least one lower layer consists of crosslinked collagen fibers in a weight quantity between 45 and 25% and hydroxylapatite in a weight quantity between 55 and 75%.

14. The cartilaginous or osteochondral substitute according to claim 1, wherein at least one lower layer consists of crosslinked collagen fibers in a weight quantity between 75 and 45% and hydroxylapatite in a weight quantity between 25 and 55% and another lower layer consists of crosslinked collagen fibers in a weight quantity between 45 and 25% and hydroxylapatite in a weight quantity between 55 and 75%.

15. The cartilaginous or osteochondral substitute according to claim 1, wherein the collagen of the crosslinked collagen fibers is selected from the group consisting of: collagen of type I, type II, type VI and mixtures thereof.

16. The cartilaginous or osteochondral substitute according to claim 1, wherein at least one lower layer consists of crosslinked collagen fibers in a weight quantity between 95 and 75% and hydroxylapatite in a weight quantity between 5 and 25%.

17. The cartilaginous or osteochondral substitute according to claim 1, wherein at least one lower layer consists of crosslinked collagen fibers in a weight quantity between 90 and 70% and hydroxylapatite in a weight quantity between 10 and 30%.

18. The cartilaginous or osteochondral substitute according to claim 1, wherein the quantity of crosslinked collagen fibers ranges down to less than 10% in the last lower layer.

* * * * *

UNITED STATES PATENT AND TRADEMARK OFFICE
CERTIFICATE OF CORRECTION

| | | |
|---|---|---|
| PATENT NO. | : 9,155,818 B2 | Page 1 of 3 |
| APPLICATION NO. | : 11/817172 | |
| DATED | : October 13, 2015 | |
| INVENTOR(S) | : Anna Tampieri | |

It is certified that error appears in the above-identified patent and that said Letters Patent is hereby corrected as shown below:

Specification

In column 1, line 4, please insert the following header:
--FIELD OF THE INVENTION--.

In column 1, between lines 17 and 18, please insert the following header:
--DESCRIPTION OF RELATED ART--.

In column 2, between lines 54 and 55, please insert the following header:
--BRIEF SUMMARY OF THE INVENTION--.

Claims

In column 17, line 27, being line 2 of claim 1, please delete "including" and insert therefor --comprising--.

In column 17, line 28, being line 3 of claim 1, please delete "consisting" and insert therefor --comprising a porous structure oriented in a vertical direction, the porous structure comprising pores and walls wherein the walls consist--.

In column 17, line 28, being line 3 of claim 1, after "fibers", please insert --oriented in a vertical direction in the walls of the pores--.

In column 17, line 30, being line 5 of claim 1, please delete "of crosslinked" and insert therefor --of a composite matrix comprising crosslinked--.

In column 17, lines 31-32, being lines 6-7 of claim 1, please delete "hydroxy-lapatite" and insert therefor --hydroxyapatite--.

Signed and Sealed this
First Day of March, 2016

Michelle K. Lee
*Director of the United States Patent and Trademark Office*

CERTIFICATE OF CORRECTION (continued)
U.S. Pat. No. 9,155,818 B2

Claims

In column 17, lines 37-38, being lines 12-13 of claim 1, please delete "characterized by" and insert therefor --wherein there is--.

In column 17, lines 39-42, being the last three lines of claim 1, please delete ", and wherein the gradient further comprises said crosslinked collagen fibers oriented in a vertical direction".

In column 18, line 1, please delete "FANS,".

In column 18, line 10, being the last line of claim 7, please delete "BDDGE" and insert therefor --1,4-butanediol-diglycidyl ether--.

In column 18, line 26, being line 2 of claim 12, please delete "consists of" and insert therefor --consists of a composite matrix comprising--.

In column 18, line 27, being line 4 of claim 12, please delete "hydroxylapatite" and insert therefor --hydroxyapatite--.

In column 18, line 31, being line 2 of claim 13, please delete "consists of" and insert therefor --consists of a composite matrix comprising--.

In column 18, line 33, being line 4 of claim 13, please delete "hydroxylapatite" and insert therefor --hydroxyapatite--.

In column 18, line 35, being line 2 of claim 14, please delete "consists of" and insert therefor --consists of a composite matrix comprising--.

In column 18, line 37, being line 4 of claim 14, please delete "hydroxylapatite" and insert therefor --hydroxyapatite--.

In column 18, line 38, being line 5 of claim 14, please delete "consists of crosslinked" and insert therefor --consists of a composite matrix comprising crosslinked--.

In column 18, line 40, being the last line of claim 14, please delete "hydroxylapatite" and insert therefor --hydroxyapatite--.

In column 18, line 46, being line 2 of claim 16, please delete "consists of" and insert therefor --consists of a composite matrix comprising--.

In column 18, line 48, being line 4 of claim 16, please delete "hydroxylapatite" and insert therefor --hydroxyapatite--.

In column 18, line 51, being line 2 of claim 17, please delete "consists of" and insert therefor --consists of a composite matrix comprising--.

Claims

In column 18, line 54, being line 4 of claim 17, please delete "hydroxylapatite" and insert therefor --hydroxyapatite--.